(12) United States Patent
Jacob et al.

(10) Patent No.: US 12,354,259 B2
(45) Date of Patent: Jul. 8, 2025

(54) SEMI-SUPERVISED LEARNING LEVERAGING CROSS-DOMAIN DATA FOR MEDICAL IMAGING ANALYSIS

(71) Applicant: SIEMENS HEALTHINEERS AG, Forchheim (DE)

(72) Inventors: Athira Jane Jacob, Plainsboro, NJ (US); Puneet Sharma, Princeton Junction, NJ (US)

(73) Assignee: Siemens Healthineers AG, Forchheim (DE)

( * ) Notice: Subject to any disclaimer, the term of this patent is extended or adjusted under 35 U.S.C. 154(b) by 483 days.

(21) Appl. No.: 17/817,363

(22) Filed: Aug. 4, 2022

(65) Prior Publication Data

US 2024/0046453 A1 Feb. 8, 2024

(51) Int. Cl.
| | |
|---|---|
| *G06T 7/00* | (2017.01) |
| *G06N 3/045* | (2023.01) |
| *G06T 7/11* | (2017.01) |
| *G16H 30/40* | (2018.01) |

(52) U.S. Cl.
CPC .......... *G06T 7/0012* (2013.01); *G06N 3/045* (2023.01); *G06T 7/11* (2017.01); *G16H 30/40* (2018.01); *G06T 2207/10088* (2013.01)

(58) Field of Classification Search
CPC ......... G06T 7/0012; G06T 7/11; G16H 30/40; G06N 3/045
See application file for complete search history.

(56) References Cited

U.S. PATENT DOCUMENTS

| | | | | |
|---|---|---|---|---|
| 2016/0133037 | A1* | 5/2016 | Vemulapalli | G06F 18/21345 382/128 |
| 2017/0039322 | A1* | 2/2017 | Reicher | G06F 16/583 |
| 2017/0186181 | A1* | 6/2017 | Sakas | G06T 7/0012 |

(Continued)

OTHER PUBLICATIONS

Hann et al., "Deep neural network ensemble for on-the-fly quality control-driven segmentation of cardiac Mri T1 mapping", Medical Image Analysis, 2021, 16 pgs.

(Continued)

*Primary Examiner* — David Bilodeau

(57) ABSTRACT

Systems and methods for performing a medical imaging analysis task are provided. An input medical image in a first modality is received. Features are extracted from the input medical image using a first machine learning based encoding network. A medical imaging analysis task is performed on the input medical image based on the extracted features by, in one embodiment, decoding the extracted features to generate results of the medical imaging analysis task using a machine learning based decoding network. Results of the medical imaging analysis task are output. In one embodiment, the first machine learning based encoding network is jointly trained with a second machine learning based encoding network with an unsupervised loss using unannotated pairs of training images. Each of the unannotated pairs comprise a first training image in the first modality and a second training image in a second modality. In one embodiment, the first machine learning based encoding network is also jointly trained with the machine learning based decoding network with a supervised loss using annotated training images.

20 Claims, 6 Drawing Sheets

(56) References Cited

U.S. PATENT DOCUMENTS

| | | | |
|---|---|---|---|
| 2022/0044105 A1* | 2/2022 | Amrani | G06N 3/088 |
| 2023/0260142 A1* | 8/2023 | Chatterjee | G06T 7/33 |
| | | | 382/154 |
| 2024/0420349 A1* | 12/2024 | Tan | G06T 7/30 |

OTHER PUBLICATIONS

Rauseo et al., "Automated myocardial segmentation in native t1-mapping cardiovascular magnetic resonance mages based on machine learning: a validation study in the UK biobanks covid-19 subset", European Heart Journal, Cardiovascular Imaging, vol. 22, Issue Supplement 2, 2021, 3 pgs.

Fahmy et al., "Automated analysis of cardiovascular magnetic resonance myocardial native T1 mapping images using fully convolutional neural networks", Journal of Cardiovascular Magnetic Resonance, 2019, 12 pgs.

\* cited by examiner

SEMI-SUPERVISED LEARNING LEVERAGING CROSS-DOMAIN DATA FOR MEDICAL IMAGING ANALYSIS

TECHNICAL FIELD

The present invention relates generally to medical imaging analysis, and in particular to semi-supervised learning leveraging cross-domain data for medical imaging analysis.

BACKGROUND

Machine learning plays an increasingly important role in the analysis of medical imaging in clinical workflows. For example, supervised deep learning techniques have shown potential for the accurate segmentation of the myocardium from magnetic resonance (MR) imaging. However, such techniques are limited by the amount of annotated data available for training machine learning algorithms. Annotations of such data is an expensive and tedious task and requires clinical expertise due to the lack of standardized protocols for contouring.

BRIEF SUMMARY OF THE INVENTION

In accordance with one or more embodiments, systems and methods are provided for semi-supervised learning leveraging cross-domain data for medical imaging analysis. Embodiments described herein utilize supervised learning using annotated training images and/or unsupervised learning using unannotated pairs of training images of different modalities.

In one embodiment, systems and methods for performing a medical imaging analysis task are provided. An input medical image in a first modality is received. Features are extracted from the input medical image using a first machine learning based encoding network. The first machine learning based encoding network is jointly trained with a second machine learning based encoding network using unannotated pairs of training images. Each of the unannotated pairs comprise a first training image in the first modality and a second training image in a second modality. A medical imaging analysis task is performed on the input medical image based on the extracted features. Results of the medical imaging analysis task are output.

In one embodiment, the first machine learning based encoding network is jointly trained with the second machine learning based encoding network using similar pairs and dissimilar pairs of the unannotated pairs of training images. The similar pairs are determined to be similar based on location and time. The location and the time are extracted from a header of the similar pairs of training images. The first machine learning based encoding network may be jointly trained with the second machine learning based encoding network with an unsupervised loss to minimize a distance between features of the similar pairs and to maximize a distance between features of the dissimilar pairs.

In one embodiment, the medical imaging analysis task is performed by decoding the extracted features to generate the results of the medical imaging analysis task using a machine learning based decoding network. The first machine learning based encoding network may be jointly trained with the machine learning based decoding network with a supervised loss using annotated training images In one embodiment, the input medical image depicts an anatomical object of a patient. The medical imaging analysis task is performed by segmenting the anatomical object from the input medical image.

In one embodiment, the first modality comprises one of cine magnetic resonance imaging (MRI), T1 mapping, or T2 mapping and the second modality comprises a different one of the cine MRI, the T1 mapping, or the T2 mapping.

These and other advantages of the invention will be apparent to those of ordinary skill in the art by reference to the following detailed description and the accompanying drawings.

DETAILED DESCRIPTION

The present invention generally relates to methods and systems for semi-supervised learning leveraging cross-domain data for medical imaging analysis. Embodiments of the present invention are described herein to give a visual understanding of such methods and systems. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

Embodiments described herein provide for a semi-supervised approach for training machine learning based networks for performing medical imaging analysis tasks, such as, e.g., segmentation, classification, detection, etc. The semi-supervised approach in embodiments described herein applies a supervised loss using annotated training images and/or an unsupervised loss using unannotated cross-modality training images for training the machine learning based networks. Advantageously, embodiments described herein may use both annotated and unannotated training images, switching losses as required.

Figure 1:
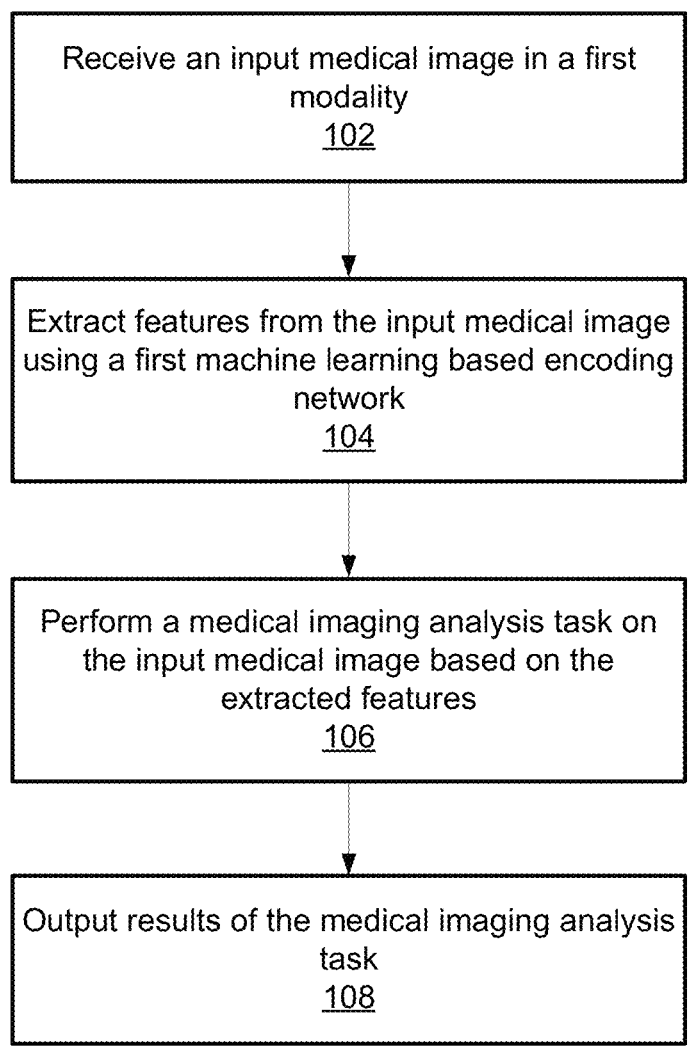
FIG. 1 shows a method for performing a medical imaging analysis task using machine learning based networks, in accordance with one or more embodiments.
Figure 2:
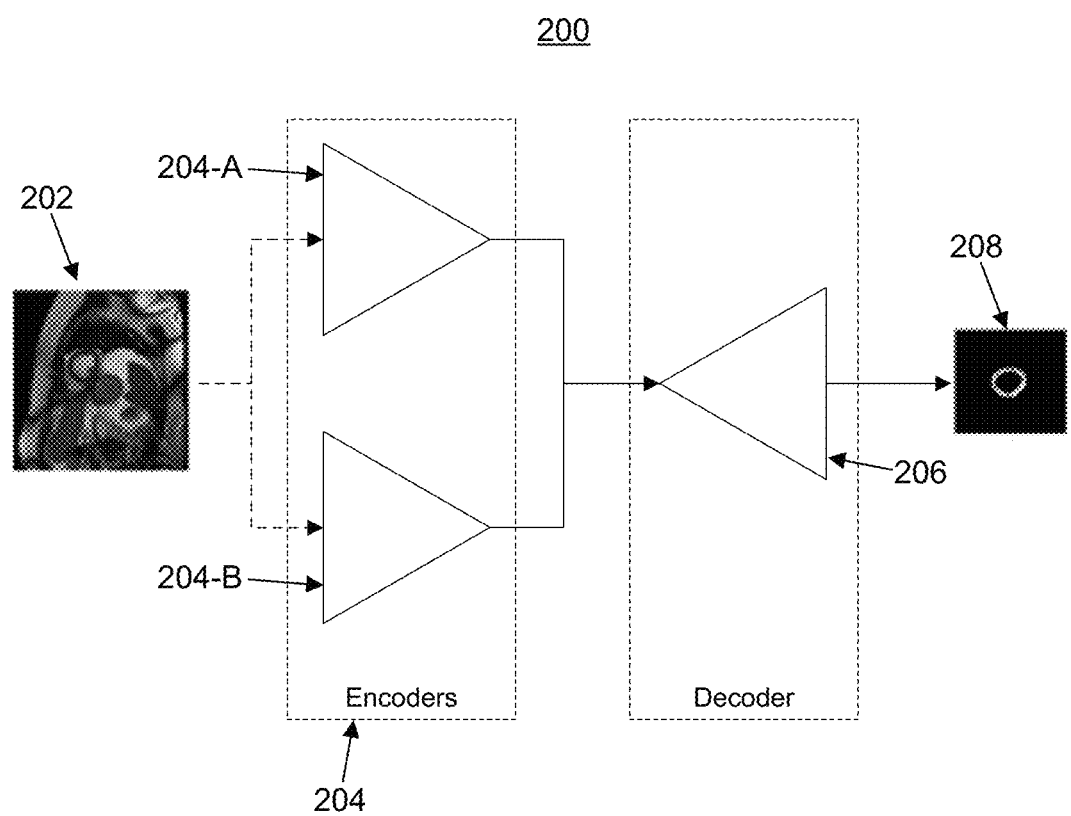
FIG. 2 shows a framework for performing the medical imaging analysis task using machine learning based networks, in accordance with one or more embodiments.

FIG. 1 shows a method 100 for performing a medical imaging analysis task using machine learning based networks, in accordance with one or more embodiments. The steps of method 100 may be performed by one or more suitable computing devices, such as, e.g., computer 602 of FIG. 6. FIG. 2 shows a framework 200 for performing the medical imaging analysis task using machine learning based networks, in accordance with one or more embodiments. FIGS. 1 and 2 will be described together.

At step 102 of FIG. 1, an input medical image in a first modality is received. The input medical image depicts an anatomical object of a patient. In one example, the anatomical object is the heart of the patient. However, the anatomical object may be any other suitable anatomical object of the patient, such as, e.g., any other organ, bone, lesion, etc. In one example, as shown in framework 200 of FIG. 2, the input medical image is input medical image 202.

In one embodiment, the first modality of the input medical image is based on magnetic resonance imaging (MRI). For example, the first modality may be cine MRI, a T1 mapping showing the T1 relaxation time for the proton (1H) magnetization in myocardial tissue of the heart, or a T2 mapping showing the T2 relaxation time for the 1H magnetization in myocardial tissue of the heart. However, the first modality may be any other suitable modality or domain, such as, e.g., computed tomography (CT), ultrasound, x-ray, or any other medical imaging modality or combinations of medical imaging modalities. The input medical image may be a 2D (two dimensional) image and/or a 3D (three dimensional) volume, and may comprise a single input medical image or a plurality of input medical images. The input medical image may be received directly from an image acquisition device, such as, e.g., an MRI scanner, as the input medical image is acquired, or can be received by loading a previously acquired medical image from a storage or memory of a computer system or receiving a medical image that has been transmitted from a remote computer system.

At step 104 of FIG. 1, features are extracted from the input medical image using a first machine learning based encoding network. In one example, as shown in framework 200, the first machine learning based encoding network is one of domain specific encoders 204-A, . . . , 204-B (collectively referred to as encoders 204). Encoders 204 may comprise any number of encoders greater than one. Each encoder 204 is a domain specific encoder that is trained for encoding images of a particular modality. Accordingly, it should be understood that only one of encoders 204 is used based on the modality of input medical image 202. Encoder 204 receives input medical image 202 as input and generates the features as output. The input of input medical image 202 into encoder 204 is represented in dashed lines in FIG. 2 to indicate that only one encoder 204 receives input medical image 202 as input. The features are latent features representing the most important features in input medical image 202.

Encoders 204 may be of any suitable machine learning based architecture. For example, encoders 204 may be the encoder network of an autoencoder, a variational autoencoder, a UNet, a DenseNet, etc. Encoders 204 are trained during a prior offline or training stage. For example, encoders 204 may be trained as discussed in further detail below with respect to FIG. 3. Once trained, the trained encoders 204 are applied during an online or inference stage to extract features from the input medical image (e.g., at step 104 of FIG. 1).

In one embodiment, the first machine learning based encoding network is jointly trained with a second machine learning based encoding network using an unsupervised loss based on unannotated pairs of training images. For example, as shown in framework 200 of FIG. 2, encoder 204-A is jointly trained with encoder 204-B (and any other encoder in encoders 204) using unannotated pairs of training images. Each of the unannotated pairs comprises a first training image in the first modality and a second training image in a second modality. The second modality may be any suitable modality different than the first modality (e.g., cine MRI, a T1 mapping, or a T2 mapping).

At step 106 of FIG. 1, a medical imaging analysis task is performed on the input medical image based on the extracted features. In one embodiment, the medical imaging analysis task is segmentation. For example, the medical imaging analysis task may be segmenting the myocardial tissue from the input medical image. However, the medical imaging analysis task may be any other suitable task performed on the input medical image, such as, e.g., classification, detection (e.g., of anatomies or pathologies), segmentation of anatomies, quantification of clinical metrics, etc.

In one embodiment, the medical imaging analysis task is performed by decoding the extracted features using a machine learning based decoding network to generate results of the medical imaging analysis task (e.g., a segmentation mask). In one example, as shown in framework 200 of FIG. 2, decoder the machine learning based decoding network is decoder 206. Decoder 206 receives the extracted features (from encoders 204) as input and generates segmentation map 208 as output.

Decoder 206 may be of any suitable machine learning based architecture. For example, decoder 206 may be the decoder network of an autoencoder, a variational autoencoder, a UNet, or any state-of-the-art decoder network. Decoder 206 is trained during a prior offline or training stage. For example, decoder 206 may be trained as discussed in further detail below with respect to FIG. 3. Once trained, the trained decoder 206 is applied during an online or inference stage to decode the extracted features and perform the medical imaging analysis task (e.g., at step 106 of FIG. 1).

In one embodiment, one or both of the first machine learning based encoding network and the second machine learning based encoding network are each respectively and jointly trained with the machine learning based decoding network using a supervised loss based on annotated training images. For example, as shown in framework 200 of FIG. 2, encoder 204-A is jointly trained with decoder 206 using annotated training images and/or encoder 204-B is jointly trained with decoder 206 using annotated training images.

At step 108 of FIG. 1, results of the medical imaging analysis task are output. For example, as shown in framework 200 of FIG. 2, segmentation map 208 is output. The results of the medical imaging analysis task can be output by, for example, displaying the results of the medical imaging analysis task on a display device of a computer system, storing the results of the medical imaging analysis task on a memory or storage of a computer system, or by transmitting the results of the medical imaging analysis task to a remote computer system.

Figure 3:
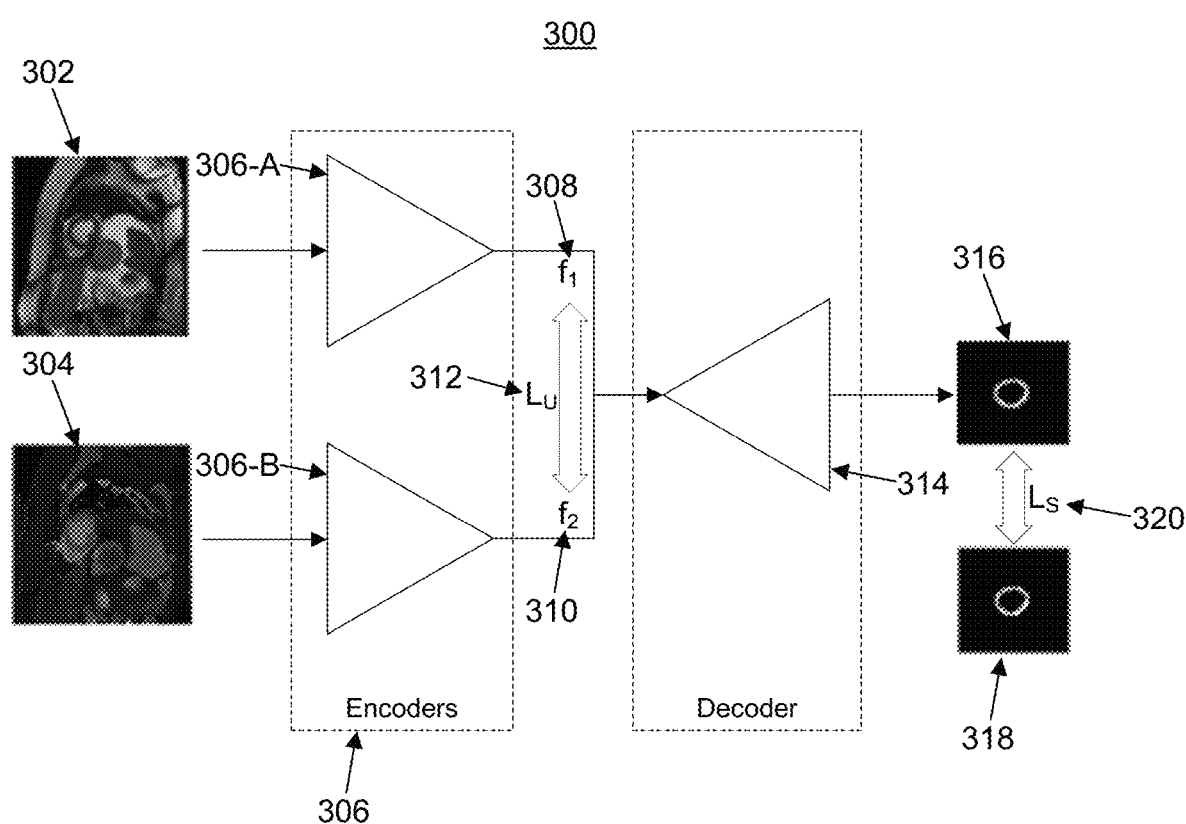
FIG. 3 shows a framework for training machine learning based networks for performing a medical imaging analysis task, in accordance with one or more embodiments.

FIG. 3 shows a framework 300 for training machine learning based networks for performing a medical imaging analysis task, in accordance with one or more embodiments. As shown in framework 300, the machine learning based networks comprise a plurality of encoders 306-A and 306-B (collectively referred to as encoders 306) and a decoder 314. Each of encoders 306 are trained for a particular modality. Framework 300 is performed to train encoders 306 and decoder 308 during a prior offline or training stage. Once trained, the trained encoders 306 and decoder 314 are applied during an online or inference stage, e.g., to perform steps 104 and 106 of method 100 of FIG. 1 respectively.

In one embodiment, encoders 206 are jointly trained with unsupervised loss $L_U$ 312 to leverage cross-modality images that may be unannotated. Encoder 306-A and 306-B respectively receive training images 302 and 304 as input and generate features $f_1$ 308 and $f_2$ 310 as output. Training images 302 and 304 are of different modalities (e.g., cine MRI, a T1 mapping, or a T2 mapping). Encoders 206 are trained with similar pairs (also called positive pairs) of training images and dissimilar pairs (also called negative pairs) of training images. In one embodiment, training images 302 and 304 are determined to be similar pairs of training images if the patient, location, and time associated with training images 302 and 304 are substantially the same or otherwise sufficiently similar (e.g., based on a threshold). The location may be the slice location (e.g., the z-location) of the image, which may be extracted from the "SliceLocation" attribute of the DICOM (digital imaging and communications in medicine) header of the image. The time may be the acquisition time of the image, which may be extracted from the "TriggerTime" attribute of the DICOM header of the image. Conversely, training images 302 and 304 are dissimilar pairs of training images if the patient, location, and/or time associated with training images 302 and 304 are not substantially the same or are not otherwise sufficiently similar. Unsupervised loss $L_U$ 312 is applied as a similarity-based metric, such as, e.g., a triplet loss, on features $f_1$ 308 and $f_2$ 310 to minimize a distance between features of similar pairs and to maximize a distance between features of dissimilar pairs by pulling similar images together and dissimilar images away in the latent space. In effect, unsupervised loss $L_U$ 312 is trained to learn smooth, similar features for the same view of anatomy, regardless of the modality. Unsupervised loss $L_U$ 312 may be defined as follows:

$$\text{Loss} = \text{Triplet Loss (similar pairs, dissimlar pairs)} = \max(0, D(\text{positive pair}) - D(\text{negative pair}) + \text{margin})$$

where D is the distance between features, such as, e.g., the L2 distance or 1-cosine (one minus cosine) similarity. In some embodiments, unsupervised loss $L_U$ 312 may be applied for annotated training images.

In one embodiment, encoders 306-A and/or 306-B are each respectively trained separately, but each encoder 306 is jointly trained with decoder 314 with supervised loss $L_S$ 320 where training images 302 and/or 304 are annotated. For example, in one supervised iteration, encoder 306-A may be jointly trained with decoder 314 and, separately, in another supervised iteration, encoder 306-B may be jointly trained with decoder 314. Decoder 314 decodes features from one of encoder 306-A or 306-B to generate segmentation map 316. Supervised loss $L_S$ 320 (e.g., cross entropy loss, dice loss, etc.) is applied to compare generated segmentation map 316 with ground truth segmentation map 318. In one embodiment, framework 300 may be implemented with a respective decoder 314 for each encoder 306 (i.e., for each modality).

Embodiments described herein leverage unannotated images of different modalities but with similar location and time for training the machine learning based networks for performing the medical imaging analysis task. In addition, embodiments described herein may leverage, e.g., cine MR images, which is a much more common modality (e.g., as compared with T1 or T2 mapping) with easier access to annotations. Embodiments described herein may utilized both annotated images and unannotated images, switching losses as required. Advantageously, embodiments described herein enable cross modality learning, resulting in more robust representations of the underlying anatomy.

In one embodiment, embodiments described herein may be applied for the joint analysis of pairs of input medical images of other modalities, such as, e.g., for the joint analysis of cine and LGE (late gadolinium enhancement) MRI images, cine and perfusion MRI images, etc.

In one embodiment, embodiments described herein may be modified and applied for the detection of image artifacts or image quality issues in the second modality.

Embodiments described herein are described with respect to the claimed systems as well as with respect to the claimed methods. Features, advantages or alternative embodiments herein can be assigned to the other claimed objects and vice versa. In other words, claims for the systems can be improved with features described or claimed in the context of the methods. In this case, the functional features of the method are embodied by objective units of the providing system.

Furthermore, certain embodiments described herein are described with respect to methods and systems utilizing trained machine learning based networks (or models), as well as with respect to methods and systems for training machine learning based networks. Features, advantages or alternative embodiments herein can be assigned to the other claimed objects and vice versa. In other words, claims for methods and systems for training a machine learning based network can be improved with features described or claimed in context of the methods and systems for utilizing a trained machine learning based network, and vice versa.

In particular, the trained machine learning based networks applied in embodiments described herein can be adapted by the methods and systems for training the machine learning based networks. Furthermore, the input data of the trained machine learning based network can comprise advantageous features and embodiments of the training input data, and vice versa. Furthermore, the output data of the trained machine learning based network can comprise advantageous features and embodiments of the output training data, and vice versa.

In general, a trained machine learning based network mimics cognitive functions that humans associate with other human minds. In particular, by training based on training data, the trained machine learning based network is able to adapt to new circumstances and to detect and extrapolate patterns.

In general, parameters of a machine learning based network can be adapted by means of training. In particular, supervised training, semi-supervised training, unsupervised training, reinforcement learning and/or active learning can be used. Furthermore, representation learning (an alternative term is "feature learning") can be used. In particular, the parameters of the trained machine learning based network can be adapted iteratively by several steps of training.

In particular, a trained machine learning based network can comprise a neural network, a support vector machine, a decision tree, and/or a Bayesian network, and/or the trained machine learning based network can be based on k-means clustering, Q-learning, genetic algorithms, and/or association rules. In particular, a neural network can be a deep neural network, a convolutional neural network, or a convolutional deep neural network. Furthermore, a neural network can be an adversarial network, a deep adversarial network and/or a generative adversarial network.

Figure 4:
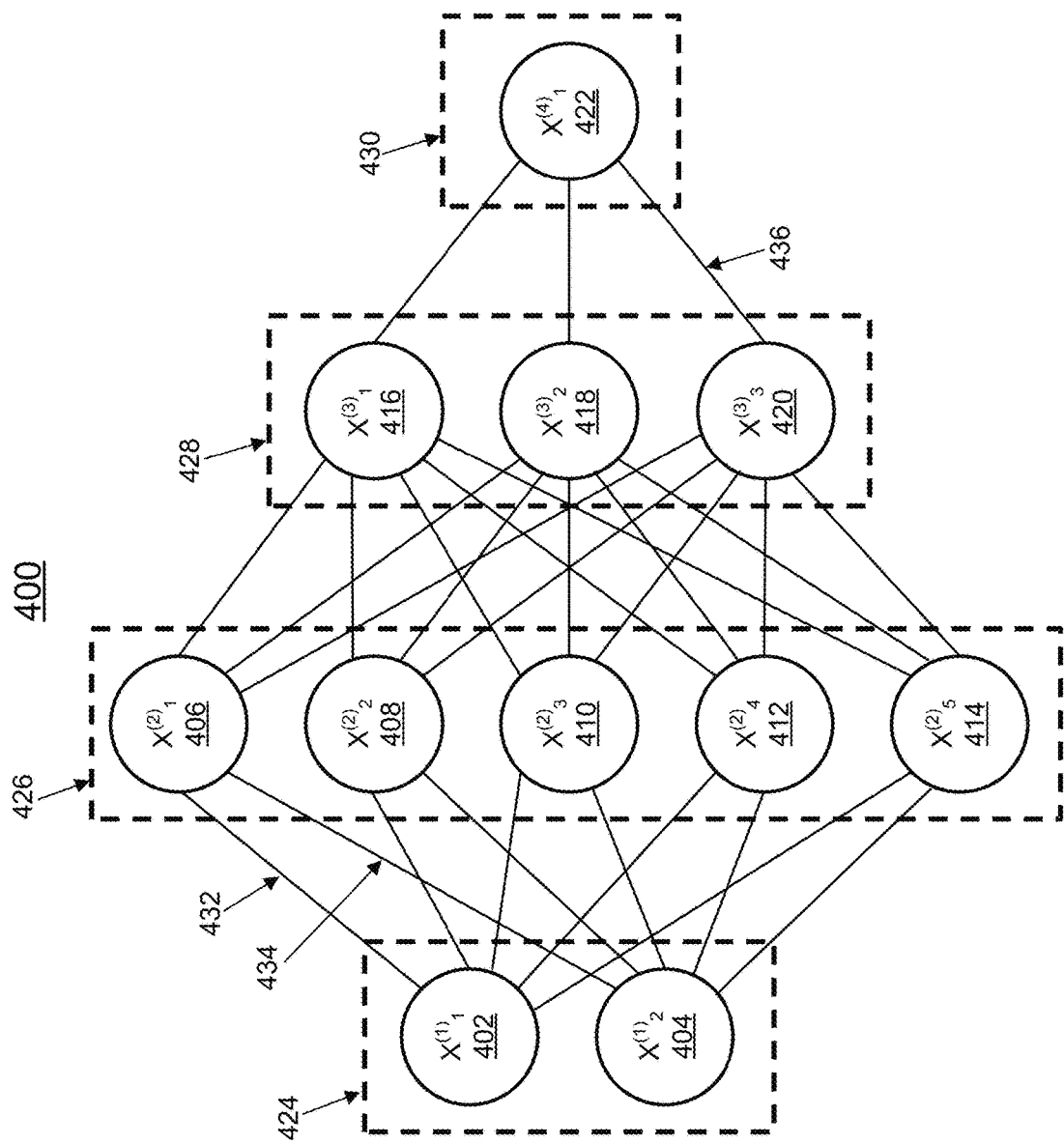
FIG. 4 shows an exemplary artificial neural network that may be used to implement one or more embodiments.

FIG. 4 shows an embodiment of an artificial neural network 400, in accordance with one or more embodiments. Alternative terms for "artificial neural network" are "neural network", "artificial neural net" or "neural net". Machine learning networks described herein, such as, e.g., the first machine learning based encoding network and the second machine learning based encoding network discussed with respect to step 104 of FIG. 1, the machine learning based decoding network discussed with respect to step 106 of FIG. 1, encoders 204 and decoder 206 of FIG. 2, and encoders 306 and decoder 314 of FIG. 3, may be implemented using artificial neural network 400.

The artificial neural network 400 comprises nodes 402-422 and edges 432, 434, . . . , 436, wherein each edge 432, 434, . . . , 436 is a directed connection from a first node 402-422 to a second node 402-422. In general, the first node 402-422 and the second node 402-422 are different nodes 402-422, it is also possible that the first node 402-422 and the second node 402-422 are identical. For example, in FIG. 4, the edge 432 is a directed connection from the node 402 to the node 406, and the edge 434 is a directed connection from the node 404 to the node 406. An edge 432, 434, . . . , 436 from a first node 402-422 to a second node 402-422 is also denoted as "ingoing edge" for the second node 402-422 and as "outgoing edge" for the first node 402-422.

In this embodiment, the nodes 402-422 of the artificial neural network 400 can be arranged in layers 424-430, wherein the layers can comprise an intrinsic order introduced by the edges 432, 434, . . . , 436 between the nodes 402-422. In particular, edges 432, 434, . . . , 436 can exist only between neighboring layers of nodes. In the embodiment shown in FIG. 4, there is an input layer 424 comprising only nodes 402 and 404 without an incoming edge, an output layer 430 comprising only node 422 without outgoing edges, and hidden layers 426, 428 in-between the input layer 424 and the output layer 430. In general, the number of hidden layers 426, 428 can be chosen arbitrarily. The number of nodes 402 and 404 within the input layer 424 usually relates to the number of input values of the neural network 400, and the number of nodes 422 within the output layer 430 usually relates to the number of output values of the neural network 400.

In particular, a (real) number can be assigned as a value to every node 402-422 of the neural network 400. Here, $x^{(n)}_i$ denotes the value of the i-th node 402-422 of the n-th layer 424-430. The values of the nodes 402-422 of the input layer 424 are equivalent to the input values of the neural network 400, the value of the node 422 of the output layer 430 is equivalent to the output value of the neural network 400. Furthermore, each edge 432, 434, . . . , 436 can comprise a weight being a real number, in particular, the weight is a real number within the interval $[-1, 1]$ or within the interval $[0, 1]$. Here, $w^{(m,n)}_{i,j}$ denotes the weight of the edge between the i-th node 402-422 of the m-th layer 424-430 and the j-th node 402-422 of the n-th layer 424-430. Furthermore, the abbreviation $w^{(n)}_{i,j}$ is defined for the weight $w^{(n,n+1)}_{i,j}$.

In particular, to calculate the output values of the neural network 400, the input values are propagated through the neural network. In particular, the values of the nodes 402-422 of the (n+1)-th layer 424-430 can be calculated based on the values of the nodes 402-422 of the n-th layer 424-430 by $$x_j^{(n+1)} = f(\Sigma_i x_i^{(n)} \cdot w_{i,j}^{(n)}).$$

Herein, the function f is a transfer function (another term is "activation function"). Known transfer functions are step functions, sigmoid function (e.g. the logistic function, the generalized logistic function, the hyperbolic tangent, the Arctangent function, the error function, the smoothstep function) or rectifier functions. The transfer function is mainly used for normalization purposes.

In particular, the values are propagated layer-wise through the neural network, wherein values of the input layer 424 are given by the input of the neural network 400, wherein values of the first hidden layer 426 can be calculated based on the values of the input layer 424 of the neural network, wherein values of the second hidden layer 428 can be calculated based in the values of the first hidden layer 426, etc.

In order to set the values $w^{(m,n)}_{i,j}$ for the edges, the neural network 400 has to be trained using training data. In particular, training data comprises training input data and training output data (denoted as $t_i$). For a training step, the neural network 400 is applied to the training input data to generate calculated output data. In particular, the training data and the calculated output data comprise a number of values, said number being equal with the number of nodes of the output layer.

In particular, a comparison between the calculated output data and the training data is used to recursively adapt the weights within the neural network 400 (backpropagation algorithm). In particular, the weights are changed according to $$w'^{(n)}_{i,j} = w^{(n)}_{i,j} - \gamma \cdot \delta^{(n)}_j \cdot x^{(n)}_i$$

wherein $\gamma$ is a learning rate, and the numbers $\delta^{(n)}_j$ can be recursively calculated as $$\delta_j^{(n)} = (\Sigma_k \delta_k^{(n+1)} \cdot w_{j,k}^{(n+1)}) \cdot f'(\Sigma_i x_i^{(n)} \cdot w_{i,j}^{(n)})$$

based on $\delta^{(n+1)}_j$, if the (n+1)-th layer is not the output layer, and $$\delta_j^{(n)} = (x_k^{(n+1)} - t_j^{(n+1)}) \cdot f'(\Sigma_i x_i^{(n)} \cdot w_{i,j}^{(n)})$$

if the (n+1)-th layer is the output layer 430, wherein f' is the first derivative of the activation function, and $y^{(n+1)}_j$ is the comparison training value for the j-th node of the output layer 430.

Figure 5:
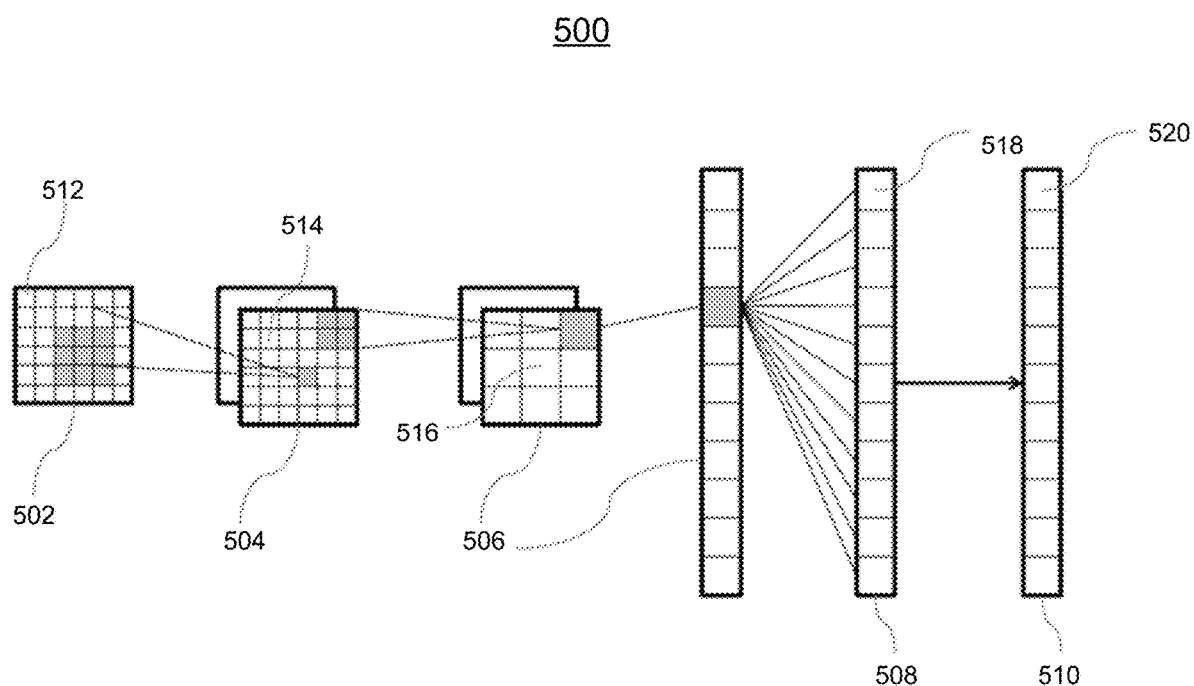
FIG. 5 shows a convolutional neural network that may be used to implement one or more embodiments.

FIG. 5 shows a convolutional neural network 500, in accordance with one or more embodiments. Machine learning networks described herein, such as, e.g., the first machine learning based encoding network and the second machine learning based encoding network discussed with respect to step 104 of FIG. 1, the machine learning based decoding network discussed with respect to step 106 of FIG. 1, encoders 204 and decoder 206 of FIG. 2, and encoders 306 and decoder 314 of FIG. 3, may be implemented using convolutional neural network 500.

In the embodiment shown in FIG. 5, the convolutional neural network comprises 500 an input layer 502, a convolutional layer 504, a pooling layer 506, a fully connected layer 508, and an output layer 510. Alternatively, the convolutional neural network 500 can comprise several convolutional layers 504, several pooling layers 506, and several fully connected layers 508, as well as other types of layers. The order of the layers can be chosen arbitrarily, usually fully connected layers 508 are used as the last layers before the output layer 510.

In particular, within a convolutional neural network 500, the nodes 512-520 of one layer 502-510 can be considered to be arranged as a d-dimensional matrix or as a d-dimensional image. In particular, in the two-dimensional case the value of the node 512-520 indexed with i and j in the n-th layer 502-510 can be denoted as $x^{(n)}_{[i,j]}$. However, the arrangement of the nodes 512-520 of one layer 502-510 does not have an effect on the calculations executed within the convolutional neural network 500 as such, since these are given solely by the structure and the weights of the edges.

In particular, a convolutional layer 504 is characterized by the structure and the weights of the incoming edges forming a convolution operation based on a certain number of kernels. In particular, the structure and the weights of the incoming edges are chosen such that the values $x^{(n)}_k$ of the nodes 514 of the convolutional layer 504 are calculated as a convolution $x^{(n)}_k = K_k * x^{(n-1)}$ based on the values $x^{(n-1)}$ of the nodes 512 of the preceding layer 502, where the convolution * is defined in the two-dimensional case as $$x_k^{(n)}[i,j]=(K_k*x^{(n-1)})[i,j]=\Sigma_{i'} \Sigma_{j'} K_k[i',j'] x^{(n-1)}[i-i',j-j'].$$

Here the k-th kernel $K_k$ is a d-dimensional matrix (in this embodiment a two-dimensional matrix), which is usually small compared to the number of nodes 512-518 (e.g. a 3×3 matrix, or a 5×5 matrix). In particular, this implies that the weights of the incoming edges are not independent, but chosen such that they produce said convolution equation. In particular, for a kernel being a 3×3 matrix, there are only 9 independent weights (each entry of the kernel matrix corresponding to one independent weight), irrespectively of the number of nodes 512-520 in the respective layer 502-510. In particular, for a convolutional layer 504, the number of nodes 514 in the convolutional layer is equivalent to the number of nodes 512 in the preceding layer 502 multiplied with the number of kernels.

If the nodes 512 of the preceding layer 502 are arranged as a d-dimensional matrix, using a plurality of kernels can be interpreted as adding a further dimension (denoted as "depth" dimension), so that the nodes 514 of the convolutional layer 504 are arranged as a (d+1)-dimensional matrix. If the nodes 512 of the preceding layer 502 are already arranged as a (d+1)-dimensional matrix comprising a depth dimension, using a plurality of kernels can be interpreted as expanding along the depth dimension, so that the nodes 514 of the convolutional layer 504 are arranged also as a (d+1)-dimensional matrix, wherein the size of the (d+1)-dimensional matrix with respect to the depth dimension is by a factor of the number of kernels larger than in the preceding layer 502.

The advantage of using convolutional layers 504 is that spatially local correlation of the input data can exploited by enforcing a local connectivity pattern between nodes of adjacent layers, in particular by each node being connected to only a small region of the nodes of the preceding layer.

In embodiment shown in FIG. 5, the input layer 502 comprises 36 nodes 512, arranged as a two-dimensional 6×6 matrix. The convolutional layer 504 comprises 72 nodes 514, arranged as two two-dimensional 6×6 matrices, each of the two matrices being the result of a convolution of the values of the input layer with a kernel. Equivalently, the nodes 514 of the convolutional layer 504 can be interpreted as arranges as a three-dimensional 6×6×2 matrix, wherein the last dimension is the depth dimension.

A pooling layer 506 can be characterized by the structure and the weights of the incoming edges and the activation function of its nodes 516 forming a pooling operation based on a non-linear pooling function f. For example, in the two dimensional case the values $x^{(n)}$ of the nodes 516 of the pooling layer 506 can be calculated based on the values $x^{(n-1)}$ of the nodes 514 of the preceding layer 504 as $$x^{(n)}[i,j]=f(x^{(n-1)}[id_1,jd_2],\ldots,x^{(n-1)}[id_1+d_1-1,jd_2+d_2-1])$$

In other words, by using a pooling layer 506, the number of nodes 514, 516 can be reduced, by replacing a number d1·d2 of neighboring nodes 514 in the preceding layer 504 with a single node 516 being calculated as a function of the values of said number of neighboring nodes in the pooling layer. In particular, the pooling function f can be the max-function, the average or the L2-Norm. In particular, for a pooling layer 506 the weights of the incoming edges are fixed and are not modified by training.

The advantage of using a pooling layer 506 is that the number of nodes 514, 516 and the number of parameters is reduced. This leads to the amount of computation in the network being reduced and to a control of overfitting.

In the embodiment shown in FIG. 5, the pooling layer 506 is a max-pooling, replacing four neighboring nodes with only one node, the value being the maximum of the values of the four neighboring nodes. The max-pooling is applied to each d-dimensional matrix of the previous layer; in this embodiment, the max-pooling is applied to each of the two two-dimensional matrices, reducing the number of nodes from 72 to 18.

A fully-connected layer 508 can be characterized by the fact that a majority, in particular, all edges between nodes 516 of the previous layer 506 and the nodes 518 of the fully-connected layer 508 are present, and wherein the weight of each of the edges can be adjusted individually.

In this embodiment, the nodes 516 of the preceding layer 506 of the fully-connected layer 508 are displayed both as two-dimensional matrices, and additionally as non-related nodes (indicated as a line of nodes, wherein the number of nodes was reduced for a better presentability). In this embodiment, the number of nodes 518 in the fully connected layer 508 is equal to the number of nodes 516 in the preceding layer 506. Alternatively, the number of nodes 516, 518 can differ.

Furthermore, in this embodiment, the values of the nodes 520 of the output layer 510 are determined by applying the Softmax function onto the values of the nodes 518 of the preceding layer 508. By applying the Softmax function, the sum the values of all nodes 520 of the output layer 510 is 1, and all values of all nodes 520 of the output layer are real numbers between 0 and 1.

A convolutional neural network 500 can also comprise a ReLU (rectified linear units) layer or activation layers with non-linear transfer functions. In particular, the number of nodes and the structure of the nodes contained in a ReLU layer is equivalent to the number of nodes and the structure of the nodes contained in the preceding layer. In particular, the value of each node in the ReLU layer is calculated by applying a rectifying function to the value of the corresponding node of the preceding layer.

The input and output of different convolutional neural network blocks can be wired using summation (residual/dense neural networks), element-wise multiplication (attention) or other differentiable operators. Therefore, the convolutional neural network architecture can be nested rather than being sequential if the whole pipeline is differentiable.

In particular, convolutional neural networks 500 can be trained based on the backpropagation algorithm. For preventing overfitting, methods of regularization can be used, e.g. dropout of nodes 512-520, stochastic pooling, use of artificial data, weight decay based on the L1 or the L2 norm, or max norm constraints. Different loss functions can be combined for training the same neural network to reflect the joint training objectives. A subset of the neural network parameters can be excluded from optimization to retain the weights pretrained on another datasets.

Systems, apparatuses, and methods described herein may be implemented using digital circuitry, or using one or more computers using well-known computer processors, memory units, storage devices, computer software, and other components. Typically, a computer includes a processor for executing instructions and one or more memories for storing instructions and data. A computer may also include, or be coupled to, one or more mass storage devices, such as one or more magnetic disks, internal hard disks and removable disks, magneto-optical disks, optical disks, etc.

Systems, apparatus, and methods described herein may be implemented using computers operating in a client-server relationship. Typically, in such a system, the client computers are located remotely from the server computer and interact via a network. The client-server relationship may be defined and controlled by computer programs running on the respective client and server computers.

Systems, apparatus, and methods described herein may be implemented within a network-based cloud computing system. In such a network-based cloud computing system, a server or another processor that is connected to a network communicates with one or more client computers via a network. A client computer may communicate with the server via a network browser application residing and operating on the client computer, for example. A client computer may store data on the server and access the data via the network. A client computer may transmit requests for data, or requests for online services, to the server via the network. The server may perform requested services and provide data to the client computer(s). The server may also transmit data adapted to cause a client computer to perform a specified function, e.g., to perform a calculation, to display specified data on a screen, etc. For example, the server may transmit a request adapted to cause a client computer to perform one or more of the steps or functions of the methods and workflows described herein, including one or more of the steps or functions of FIG. 1. Certain steps or functions of the methods and workflows described herein, including one or more of the steps or functions of FIG. 1, may be performed by a server or by another processor in a network-based cloud-computing system. Certain steps or functions of the methods and workflows described herein, including one or more of the steps of FIG. 1, may be performed by a client computer in a network-based cloud computing system. The steps or functions of the methods and workflows described herein, including one or more of the steps of FIG. 1, may be performed by a server and/or by a client computer in a network-based cloud computing system, in any combination.

Systems, apparatus, and methods described herein may be implemented using a computer program product tangibly embodied in an information carrier, e.g., in a non-transitory machine-readable storage device, for execution by a programmable processor; and the method and workflow steps described herein, including one or more of the steps or functions of FIG. 1, may be implemented using one or more computer programs that are executable by such a processor. A computer program is a set of computer program instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Figure 6:
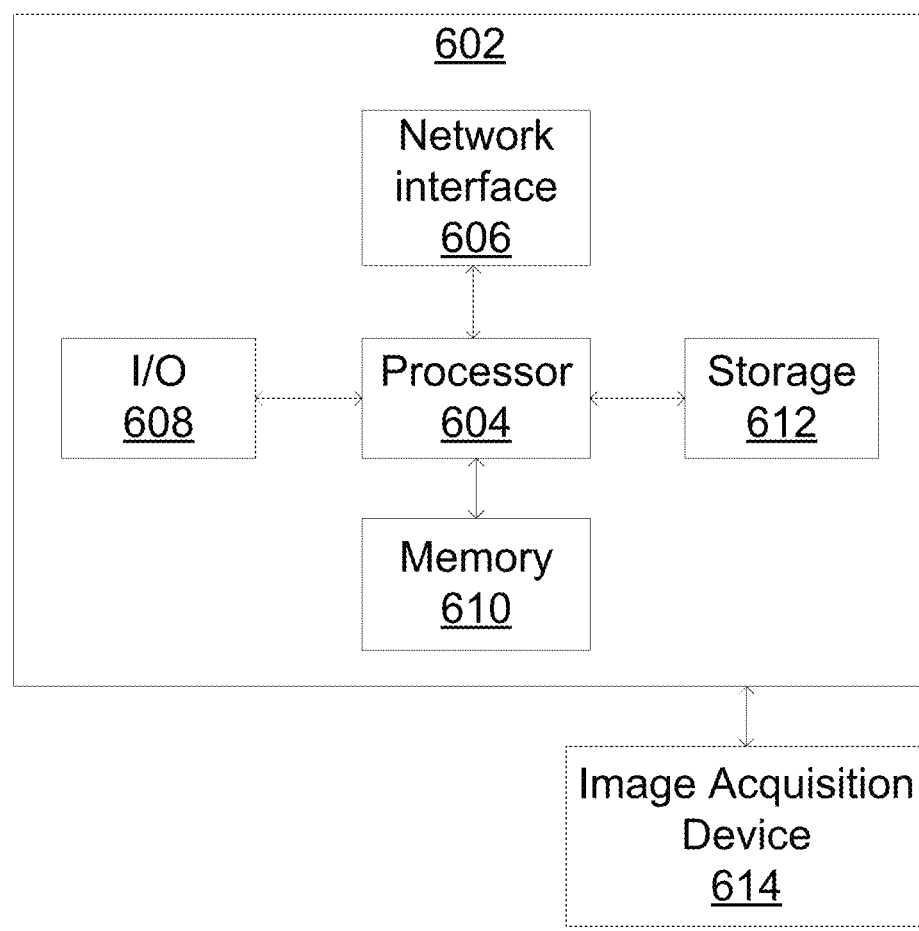
FIG. 6 shows a high-level block diagram of a computer that may be used to implement one or more embodiments.

A high-level block diagram of an example computer 602 that may be used to implement systems, apparatus, and methods described herein is depicted in FIG. 6. Computer 602 includes a processor 604 operatively coupled to a data storage device 612 and a memory 610. Processor 604 controls the overall operation of computer 602 by executing computer program instructions that define such operations. The computer program instructions may be stored in data storage device 612, or other computer readable medium, and loaded into memory 610 when execution of the computer program instructions is desired. Thus, the method and workflow steps or functions of FIG. 1 can be defined by the computer program instructions stored in memory 610 and/or data storage device 612 and controlled by processor 604 executing the computer program instructions. For example, the computer program instructions can be implemented as computer executable code programmed by one skilled in the art to perform the method and workflow steps or functions of FIG. 1. Accordingly, by executing the computer program instructions, the processor 604 executes the method and workflow steps or functions of FIG. 1. Computer 602 may also include one or more network interfaces 606 for communicating with other devices via a network. Computer 602 may also include one or more input/output devices 608 that enable user interaction with computer 602 (e.g., display, keyboard, mouse, speakers, buttons, etc.).

Processor 604 may include both general and special purpose microprocessors, and may be the sole processor or one of multiple processors of computer 602. Processor 604 may include one or more central processing units (CPUs), for example. Processor 604, data storage device 612, and/or memory 610 may include, be supplemented by, or incorporated in, one or more application-specific integrated circuits (ASICs) and/or one or more field programmable gate arrays (FPGAs).

Data storage device 612 and memory 610 each include a tangible non-transitory computer readable storage medium. Data storage device 612, and memory 610, may each include high-speed random access memory, such as dynamic random access memory (DRAM), static random access memory (SRAM), double data rate synchronous dynamic random access memory (DDR RAM), or other random access solid state memory devices, and may include non-volatile memory, such as one or more magnetic disk storage devices such as internal hard disks and removable disks, magneto-optical disk storage devices, optical disk storage devices, flash memory devices, semiconductor memory devices, such as erasable programmable read-only memory (EPROM), electrically erasable programmable read-only memory (EEPROM), compact disc read-only memory (CD-ROM), digital versatile disc read-only memory (DVD-ROM) disks, or other non-volatile solid state storage devices.

Input/output devices 608 may include peripherals, such as a printer, scanner, display screen, etc. For example, input/output devices 608 may include a display device such as a cathode ray tube (CRT) or liquid crystal display (LCD) monitor for displaying information to the user, a keyboard, and a pointing device such as a mouse or a trackball by which the user can provide input to computer 602.

An image acquisition device 614 can be connected to the computer 602 to input image data (e.g., medical images) to the computer 602. It is possible to implement the image acquisition device 614 and the computer 602 as one device. It is also possible that the image acquisition device 614 and the computer 602 communicate wirelessly through a network. In a possible embodiment, the computer 602 can be located remotely with respect to the image acquisition device 614.

Any or all of the systems and apparatus discussed herein may be implemented using one or more computers such as computer 602.

One skilled in the art will recognize that an implementation of an actual computer or computer system may have other structures and may contain other components as well, and that FIG. 6 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A computer-implemented method comprising:
receiving an input medical image in a first modality;
extracting features from the input medical image using a first machine learning based encoding network, wherein the first machine learning based encoding network is jointly trained with a second machine learning based encoding network using unannotated pairs of training images, each of the unannotated pairs comprising a first training image in the first modality and a second training image in a second modality;
performing a medical imaging analysis task on the input medical image based on the extracted features; and
outputting results of the medical imaging analysis task.

2. The computer-implemented method of claim 1, wherein the first machine learning based encoding network is jointly trained with the second machine learning based encoding network using similar pairs and dissimilar pairs of the unannotated pairs of training images.

3. The computer-implemented method of claim 2, wherein the similar pairs are determined to be similar based on location and time.

4. The computer-implemented method of claim 3, wherein the location and the time are extracted from a header of the similar pairs of training images.

5. The computer-implemented method of claim 2, wherein the first machine learning based encoding network is jointly trained with the second machine learning based encoding network with an unsupervised loss to minimize a distance between features of the similar pairs and to maximize a distance between features of the dissimilar pairs.

6. The computer-implemented method of claim 1, wherein performing a medical imaging analysis task on the input medical image based on the extracted features comprises:
decoding the extracted features to generate the results of the medical imaging analysis task using a machine learning based decoding network.

7. The computer-implemented method of claim 6, wherein the first machine learning based encoding network is jointly trained with the machine learning based decoding network with a supervised loss using annotated training images.

8. The computer-implemented method of claim 1, wherein the input medical image depicts an anatomical object of a patient and performing a medical imaging analysis task on the input medical image based on the extracted features comprises:
segmenting the anatomical object from the input medical image.

9. The computer-implemented method of claim 1, wherein the first modality comprises one of cine magnetic resonance imaging (MRI), T1 mapping, or T2 mapping and the second modality comprises a different one of the cine MRI, the T1 mapping, or the T2 mapping.

10. An apparatus comprising:
means for receiving an input medical image in a first modality;
means for extracting features from the input medical image using a first machine learning based encoding network, wherein the first machine learning based encoding network is jointly trained with a second machine learning based encoding network using unannotated pairs of training images, each of the unannotated pairs comprising a first training image in the first modality and a second training image in a second modality;
means for performing a medical imaging analysis task on the input medical image based on the extracted features; and
means for outputting results of the medical imaging analysis task.

11. The apparatus of claim 10, wherein the first machine learning based encoding network is jointly trained with the second machine learning based encoding network using similar pairs and dissimilar pairs of the unannotated pairs of training images.

12. The apparatus of claim 11, wherein the similar pairs are determined to be similar based on location and time.

13. The apparatus of claim 12, wherein the location and the time are extracted from a header of the similar pairs of training images.

14. The apparatus of claim 11, wherein the first machine learning based encoding network is jointly trained with the second machine learning based encoding network with an unsupervised loss to minimize a distance between features of the similar pairs and to maximize features of the dissimilar pairs.

15. A non-transitory computer readable medium storing computer program instructions, the computer program instructions when executed by a processor cause the processor to perform operations comprising:
receiving an input medical image in a first modality;
extracting features from the input medical image using a first machine learning based encoding network, wherein the first machine learning based encoding network is jointly trained with a second machine learning based encoding network using unannotated pairs of training images, each of the unannotated pairs comprising a first training image in the first modality and a second training image in a second modality;
performing a medical imaging analysis task on the input medical image based on the extracted features; and
outputting results of the medical imaging analysis task.

16. The non-transitory computer readable medium of claim 15, wherein the first machine learning based encoding network is jointly trained with the second machine learning based encoding network using similar pairs and dissimilar pairs of the unannotated pairs of training images.

17. The non-transitory computer readable medium of claim 15, wherein performing a medical imaging analysis task on the input medical image based on the extracted features comprises:
decoding the extracted features to generate the results of the medical imaging analysis task using a machine learning based decoding network.

18. The non-transitory computer readable medium of claim 17, wherein the first machine learning based encoding network is jointly trained with the machine learning based decoding network with a supervised loss using annotated training images.

19. The non-transitory computer readable medium of claim 15, wherein the input medical image depicts an anatomical object of a patient and performing a medical imaging analysis task on the input medical image based on the extracted features comprises:

segmenting the anatomical object from the input medical image.

20. The non-transitory computer readable medium of claim 15, wherein the first modality comprises one of cine magnetic resonance imaging (MRI), T1 mapping, or T2 mapping and the second modality comprises a different one of the cine MRI, the T1 mapping, or the T2 mapping.

\* \* \* \* \*